US007114249B2

(12) United States Patent
Murakami (10) Patent No.: US 7,114,249 B2
(45) Date of Patent: Oct. 3, 2006

(54) SUBSTRATE INSPECTING METHOD AND SUBSTRATE INSPECTING APPARATUS USING THE METHOD (75) Inventor: Kiyoshi Murakami, Fukuchiyama (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/786,468

(22) Filed: Feb. 26, 2004

(65) Prior Publication Data
US 2004/0208353 A1 Oct. 21, 2004

(30) Foreign Application Priority Data
Feb. 27, 2003 (JP) ............... 2003-050357

(51) Int. Cl.
H05K 3/30 (2006.01)
(52) U.S. Cl. ............... 29/833; 29/825; 29/832; 29/840; 702/84
(58) Field of Classification Search ........... 29/832, 29/833, 840, 825; 702/84, 95
See application file for complete search history.

(56) References Cited

U.S. PATENT DOCUMENTS

| 4,737,845 | A | * | 4/1988 | Susuki et al. ............. 348/87 |
| 4,914,808 | A | * | 4/1990 | Okumura et al. ............. 29/740 |
| 5,084,962 | A | * | 2/1992 | Takahashi et al. ............. 29/833 |
| 5,235,407 | A | * | 8/1993 | Spigarelli et al. ............. 356/399 |
| 5,251,266 | A | * | 10/1993 | Spigarelli et al. ............. 382/151 |
| 5,471,310 | A | * | 11/1995 | Spigarelli et al. ............. 356/399 |
| 5,926,950 | A | * | 7/1999 | Asai et al. ............. 29/832 |
| 6,260,260 | B1 | * | 7/2001 | Suhara ............. 29/740 |
| 6,538,425 | B1 | * | 3/2003 | Kawada ............. 324/158.1 |
| 6,688,016 | B1 | * | 2/2004 | Suhara et al. ............. 33/613 |
| 6,739,036 | B1 | * | 5/2004 | Koike et al. ............. 29/743 |
| 6,769,172 | B1 | * | 8/2004 | Suhara et al. ............. 29/740 |
| 6,850,855 | B1 | * | 2/2005 | Kawai et al. ............. 702/84 |
| 6,861,269 | B1 | * | 3/2005 | Kawai et al. ............. 438/14 |
| 6,931,716 | B1 | * | 8/2005 | Suhara et al. ............. 29/740 |
| 6,941,646 | B1 | * | 9/2005 | Suhara ............. 29/740 |
| 6,999,835 | B1 | * | 2/2006 | Kodama ............. 700/121 |

FOREIGN PATENT DOCUMENTS

EP 0 718 623 A2 6/1996
JP 2002-183712 A 6/2002

(Continued)

OTHER PUBLICATIONS

E. Kamen et al., Analysis of Factors Affecting Component Placment Accuracy In SMT Electronics Assembly, 1998 IEEE/CPMT Int'l Electronics Technology Symposium, pp. 50-57.

(Continued)

Primary Examiner—Carl J. Arbes
(74) Attorney, Agent, or Firm—Foley & Lardner LLP (57) ABSTRACT Inspection a is executed between a step B of mounting a chip component by a high-speed mounter and a step C of mounting a odd-shaped component by a odd-shape mounter. The inspection a executes not only mounted component inspection for determining a mounted state of a chip component mounted in the preceding step but also component fly inspection for determining whether a chip component is flown to a position where a odd-shaped component is mounted in the next step C. It is possible to execute the component fly inspection in accordance with a condition corresponding to the situation of an actual spot such as a case in which it is detected that a component is missing in mounted component inspection or a case in which the replacement date of an attracting nozzle in a high-speed mounter is approaching.

15 Claims, 7 Drawing Sheets

FOREIGN PATENT DOCUMENTS

JP  2002 271099  9/2002

OTHER PUBLICATIONS

E. Kamen et al., "Monitoring Surface-Mount Component Placement," Circuits Assembly, 10:1, Jan. 1991, pp. 42, 44, 46-49, XP-002287410.

E.K. Teoh et al., "An Intelligent Robotic Vision System for Inspection of Surface Mount PCBs," Proceedings of the Int'l Conference on Systems, vol. 1, Oct. 13, 1991, pp. 13-17, XP-010054964.

J.J. Tepe, "Automated Vision Inspection for the Component Assembly Process," Automotive Engineering, Society of Auto. Engineers, vol. 104, No. 9, pp. 8-15, XP-000627058.

* cited by examiner

SUBSTRATE INSPECTING METHOD AND SUBSTRATE INSPECTING APPARATUS USING THE METHOD

BACKGROUND OF THE INVENTION

1. Field of the Invention

The present invention relates to a technical field for inspecting a printed circuit board (hereafter referred to as "component mounting substrate" or simply referred to as "substrate") with components mounted. Particularly, the present invention relates to an apparatus having a function for executing an inspecting method to be executed between a first component mounting step and a second component mounting step in a fabricating line in which mounting a component is executed in two separate stages and a function for executing the inspecting method.

2. Description of the Prior Art

A component mounting machine referred to as "mounter" has been used so far in order to automate high-density component mounting. Conventional mounters include a mounter (generally referred to as "high-speed mounter") having a function for mounting a small component such as a chip component at a high speed and a mounter (generally referred to as "odd-shape mounter") for mounting odd-shaped components such as BGA, CSP, and IC.

In the case of a conventional general substrate fabricating line, processing of printing cream solder on a bare substrate is first performed in a solder printing machine and then the substrate is sent to a high-speed mounter and an odd-shape mounter in order to mount the above various components. Moreover, the substrate after mounting components is sent to a reflow furnace to undergo soldering.

A substrate inspecting apparatus is properly set to the rear stage of each mounter. The substrate inspecting apparatus inspects a cream-solder printed state on a substrate and whether components are correctly mounted on component mounting positions and only substrates passing the inspection are sent to the reflow furnace.

For example, a technique is disclosed in Japanese Patent Laid-Open Publication No. 2002-183712 as a prior art showing this type of inspection. In Japanese Patent Laid-Open Publication No. 2002-183712, an image of a character string printed on the main portion of a component is extracted from an image obtained by imaging a substrate to be inspected to recognize the characters and thereby it is determined whether a correct component is mounted.

The high-speed mounter repeatedly executes processing of attracting a component supplied from a component supplying device by an attracting nozzle, processing of carrying the attracted component up to a component mounting position, and processing of releasing the attracted component at the component mounting position. A component may be flown to a position different from the original mounting position (this phenomenon is hereafter referred to as "component fly").

A component is flown due to various factors. It is considered as the most possible factor that a component is attracted in an unstable state due to abrasion of an attracting nozzle and dropped before it reaches a mounting position. Moreover, two components are simultaneously attracted by an attracting nozzle and one of them may be dropped to a position different from the original mounting position or while the attracting nozzle carries a component or when mounting the component, the component may contact with other component and the other component may fly to other position.

Furthermore, component fly may occur also when an air pressure or attraction time for attracting a component is incorrectly set and thereby the timing for canceling the attraction of the component becomes incorrect or a component size is not fitted to the diameter of a nozzle because an incorrect component is supplied to a component supplying device.

Furthermore, when cream solder falls short because a mask clogs or a squeezee is abraded, the adhesive strength of the solder decreases. Therefore, when a component is carried to the next step after mounted, the component may fly due to the force of carrying the component.

Thus, when component fly occurs in a high-speed mounter, the flown component drops to a mounting position of the odd-shaped component, and under this state, a substrate is sent to a odd-shape mounter, the odd-shaped component is mounted on the flown component and thereby, a trouble may occur.

SUMMARY OF THE INVENTION

The present invention is made to solve the above problem and its object is to quickly detect this type of component fly so that a second component mounting step is not influenced by inspecting whether a component mounted in a first component mounting step is flown to a component mounting position in a second component mounting step after the first component mounting step is completed.

A substrate inspecting method of the present invention is executed between a first component mounting step of mounting a predetermined type of component on a printed circuit board and a second component mounting step of mounting a component on a position on which no component is mounted in the first component mounting step. A first inspecting method of the present invention inspects whether a component mounted in the first component mounting step is included in a region corresponding to the component mounting position in the second component mounting step on a substrate undergoing the first component mounting step.

The above inspection can be performed by processing of imaging a substrate to be inspected and determining on an image obtained in the second component mounting step whether the image of a component to be mounted in a first component mounting step is included in a region corresponding to the component mounting position. The determination in the above case can be performed by processing of digitizing an image in a region corresponding to the component mounting position by a preset threshold value, extracting an image pattern having a characteristic value corresponding to a component (for example, extracting a pattern having the same color as a component in the case of a color image), and collating a characteristic value such as the size or shape of the extracted image pattern with a model value preset as a characteristic value adapted for a component.

According to the above method, when a component is flown to the component mounting position in a second component mounting step to be next executed in a first component mounting step, it is possible to detect the component. Therefore, by removing the flown component or identifying a defective substrate, it is possible to sort components or substrates later and avoid that a trouble due to component fly is overlooked.

Then, a second substrate inspecting method of the present invention executes processing of imaging a substrate undergoing a first component mounting step whenever accepting the substrate, first inspection for determining on an obtained image whether the image of a component is included in a region corresponding to the component mounting position in the first component mounting step, and second inspection for determining whether the image of a component mounted in the first component mounting step is included in a region corresponding to the component mounting position in a second component mounting step.

The first and second inspections can respectively determine the image of a component or not in accordance with processing of collating the characteristic value of an image pattern extracted through digitization with the model value of a predetermined characteristic value same as the case of the description for the first inspecting method in an image obtained by imaging a substrate to be inspected.

In the case of the first inspection, determination of "component present" denotes that an inspection result is "good". However, in the case of the second inspection, determination of "component present" denotes that an inspection result is "bad". In the case of the first and second inspections, when a good determination is obtained, it is possible to determine that a substrate to be inspected is a good product.

According to the above inspecting method, when inspecting on all substrates undergoing a first component mounting step whether a purposed component in the step is correctly mounted, it is inspected whether component fly occurs in a region to be processed in a second component mounting step. Therefore, even if component fly occurs due to a factor which cannot be predicted, it is possible to accurately detect the component fly.

Moreover, as described above, to execute first and second inspections, it is possible to execute the inspections in order by executing the first inspection and then executing the second inspection. However, when imaging an object a plurality of times while changing imaging positions, it is preferable to process a region included in the image of the object for the first inspection and a region included in the object of the image for the second inspection in a proper sequence whenever imaging the object. The same is applied to fourth and fifth inspecting method to be described later.

In the case of third to fifth substrate inspecting methods, second inspection is executed when a predetermined condition is effected. First, in the case of the third inspecting method, whenever accepting a substrate undergoing the first component mounting step, processing of imaging the substrate and first inspection same as described above are executed and when it is determined in the first inspection that the image of a component is not correctly included in a predetermined region, the second inspection is executed.

The above method can correspond to a case in which a component is dropped due to a defective attracting nozzle while it is carried or a component is not properly mounted but it flies to a position on which a component will be mounted in a near second component mounting step. According to the above method, for example, when missing of a component is detected at the component mounting position in a first component mounting step through the first inspection, it is possible to execute the second inspection. Therefore, when the missing component flies to a position where a component will be mounted in a second component mounting step, the trouble can be detected. Therefore, it is possible to efficiently detect component fly caused by a high-frequency factor.

The fourth inspecting method executes the following: processing of imaging a substrate undergoing a first component mounting step whenever accepting the substrate while it is possible to accept the information showing the expiry date of an implement for mounting a component used in a first component mounting step and first inspection for determining on an obtained image whether the image of a component is included in a region corresponding to the component mounting position in the first component mounting step. Moreover, the fourth inspecting method executes second inspection for determining on a predetermined number of substrates to be accepted later whether the image of a component mounted in the first component mounting step is included in a region corresponding to the component mounting position in the second component mounting step together with the imaging and first inspection.

In the above description, the component-mounting implement is an attracting nozzle of a mounter for executing the first component mounting step or an implement conforming to the attracting nozzle. It is preferable to obtain the information showing the expiry date of the implement as the information transmitted from the mounter. Because the mounter can obtain the operating frequency of the attracting nozzle by using a method of counting the operating frequency of a nozzle since it was replaced, it is possible to accurately transmit the nozzle replacing date to an inspecting apparatus.

However, information to be accepted is not restricted to the above information. For example, it is also allowed to accept the information manually input by a person in charge of determining the operating frequency of the attracting nozzle.

The above inspecting method executes only the first inspection for a substrate supplied every time. However, when information is input, the inspection method changes the state and executes the first and second inspections for a predetermined number of substrates to be subsequently supplied. When this type of information is read to output, it is estimated that the probability of component fly is high because the probability that a trouble occurs in attraction of or cancellation of the attraction of a component is very high. Therefore, the fourth inspecting method makes it possible to efficiently and accurately detect component fly due to abrasion of the implement.

It is preferable to set the above information as advance notice information showing that replacement date of an attracting nozzle is approaching before the nozzle becomes an inoperable state. In this case, it is possible to estimate the number of substrates to be sent to the first component mounting step before the attracting nozzle is replaced with a new one after the information is output and execute first and second inspection for the number of substrates obtained by providing a predetermined allowance for the estimated number of substrates. Or, it is allowed to estimate the time until the attracting nozzle is replaced after the information is output and execute first and second inspections for the substrates supplied in the estimated time.

However, to perform inspections more securely, it is preferable to execute first and second inspections for at least substrates supplied before accepting the information showing that the component replacing implement is replaced from a mounter. Moreover, it is preferable that the information showing that replacement of the implement is completed is output in accordance with the replacement completion operation executed after a user confirms that a component attracting force is proper after replacing the implement. It is more preferable to execute both the first and second inspections for the number of substrates which may be put between the mounter and the inspecting apparatus when accepting the information.

The fifth substrate inspecting method of the present invention executes processing of imaging a substrate undergoing the first component mounting step and the first inspection whenever accepting the substrate under a state capable of accepting information showing that the printed state of solder of a substrate sent to the first component mounting step is deteriorated. Moreover, correspondingly to input of the information, the second inspection is executed for a predetermined number of substrates to be subsequently accepted together with the processing of imaging the substrate and the first inspection.

The fifth inspecting method can correspond to a case in which chip fly may occur due to defectiveness of solder printing in a solder printing step. It is possible to transmit the information input by the above method from a solder printing machine as a signal for previously notifying a person of the replacement date of an implement such as the above squeezee or mask from, for example, a solder printing machine.

It is possible to set even the fifth inspecting method so as to execute first and second inspections for a previously assumed number of substrates or substrates supplied by an assumed time passes. However, to execute more accurate inspection, it is recommended to set the method so as to execute first and second inspections for each substrate supplied by the time when the above information is input, more preferably by the time when a predetermined number of substrates are supplied after the information is input. Moreover, it is preferable that a signal showing that replacement of implements is completed is output correspondingly to the operation performed when a user confirms that the solder printing state after replacing implements is proper and then applies the replacement completion operation to the solder printing machine.

In the case of each inspecting method described above, it is possible to set a step of mounting a chip component as a first component mounting step. Moreover, it is possible to set a step of mounting a odd-shaped component as a second component mounting step.

It is possible to execute the first component mounting step by a high-speed mounter and the second component mounting step by a odd-shape mounter. Moreover, it is possible to use a mounter referred to as "modular-type mounter" in each component mounting step. Particularly, because the processing same as the case of the high-speed mounter is performed in the first component mounting step, a plurality of modular-type mounters may be used. In this case, however, it is preferable to execute each of the above inspecting methods for a substrate passing through the final mounter in the first component mounting step.

Moreover, in the first component mounting step, it is possible to mount not only a chip component but also small components such as a transistor, melf, and tartar capacitor. Moreover, as odd-shaped components purposed by the second component mounting step, it is possible to mount a plurality of components different from each other in shape and size such as not only the above BGA, CSP, and IC but also a filter, connector, coil, PLCC (plastic IC package), discrete substrate, shielding case, and earth spring. Moreover, in some cases, it is also possible to mount a chip component.

Furthermore, in the case of each of the above inspecting methods, an object of the inspection for component fly is not restricted to the component mounting position in the second component mounting step. For example, it is also allowed to inspect the whole substrate excluding the component mounting position in the first component mounting step.

Then, a substrate inspecting apparatus of the present invention is set between the above first component mounting step and second component mounting step to inspect the component mounted state of a substrate undergoing the first component mounting step. The apparatus is provided with an imaging part for imaging a substrate to be inspected, inspection data for executing the first inspection for an image obtained by the imaging part, a storing part for storing the inspection data for executing the first inspection and the inspection data for executing the second inspection, an inputting part for inputting a condition for executing the second inspection, an inspection executing part for processing the image obtained by the imaging part by using the inspection data for the first inspection and processing the image by using the inspection data for the second inspection when the condition input from the inputting part is effected, and an outputting part for outputting a result of the inspection by the inspection executing part.

Moreover, it is preferable to set a stage for supporting a substrate to be inspected and a light source for illumination to the inspecting apparatus. Furthermore, it is preferable to set an imaging part or stage, or a mechanism (such as XY table) for adjusting positions of the imaging part and stage so that a relative positional relation between an imaging part and a substrate can be changed.

Furthermore, in the case of the inspecting apparatus, to execute the fourth and fifth inspecting methods, it is preferable to accept the information showing the expiry date of an implement for mounting a component used in a first component mounting step and the information showing that the printed state of solder of a substrate sent to the first component mounting step is deteriorated by using a part for performing communication with an external apparatus such as a mounter or solder printing machine.

It is preferable that the imaging part can generate a color image. Moreover, without being restricted to the above mentioned, it is possible to use a camera for generating a monochrome image.

A storing part for storing inspection data can be set to a memory in a computer. It is possible to include set data of an inspecting window, a parameter for extracting a component image (such as the above threshold value for digitization), and a criterion value (such as the above model value of characteristic value) for determining presence or absence of a component in the inspection data related to first and second inspections stored in the storing part and moreover, include a program showing an inspection procedure according to necessity. These inspection data values can be generated in an apparatus by imaging a model substrate, setting an inspecting window to each portion to be inspected on the image of the model substrate, and designating an image region having a characteristic value to be extracted in the window. Moreover, without being restricted to the above mentioned, it is possible to transplant inspection data generated by an external device into an apparatus by using communication and a recording medium.

An inspection executing part can be constituted by introducing a program for reading inspection data from the storing part for execution into a computer in which a storing part is set.

The above inputting part can be used as a keyboard or console connected to the above computer. Moreover, the inputting part can include a user interface by the program set to the computer.

An outputting part can be used as an interface circuit for accepting an inspection result from the inspection executing part and outputting it to an external device or display device.

Moreover, it is possible to constitute the external device as a conveyer for carrying a substrate and the outputting part as a part for outputting a stop signal to the conveyer when an inspection result shows "no good".

Furthermore, an outputting part can be constituted as a part for storing an inspection result in a predetermined storing medium or a part for executing warning processing such as sounding an alarm.

In the case of the above inspecting apparatus, the inspection executing part executes first inspection for an image obtained by the imaging part without fail and moreover executes second inspection when a condition input from the inputting part is effected.

It is possible to set, for example, the expression that no-good determination is made through first inspection as the condition input from the inputting part. Moreover, it is possible to set the expression that the expiry date of a component mounting implement is approaching or the solder state of a substrate sent to a first component mounting step is deteriorated as the condition input from the inputting part.

When using the expression that no-good determination is made through first inspection as a condition, it is possible to execute the third inspecting method. Therefore, when a component to be mounted in the first component mounting step is missing in a supplied substrate and the component flies to a position where a component will be mounted in a second component mounting step, it is possible to detect the component fly.

Moreover, when using the expression that the expiry date of a component mounting implement is approaching as a condition, it is possible to execute the fourth inspecting method and when using the expression that the solder state is deteriorated as a condition, execute the fifth inspecting method. Therefore, under a state in which component fly easily occurs due to abrasion of an implement in a mounter or solder printing machine, it is possible to execute second inspection for detecting component fly.

Moreover, it is possible to set the expression that "every substrate is used as an object of second inspection" as a predetermined condition. In this case, first and second inspections are executed whenever a substrate is imaged in accordance with the second inspecting method.

According to the above substrate inspecting apparatus, it is possible to set a condition correspondingly to a main factor in which component fly occurs and execute second inspection when the condition is effected. Therefore, it is possible to efficiently and accurately detect component fly correspondingly to the state of the actual spot.

DESCRIPTION OF THE PREFERRED EMBODIMENTS

Figure 1:
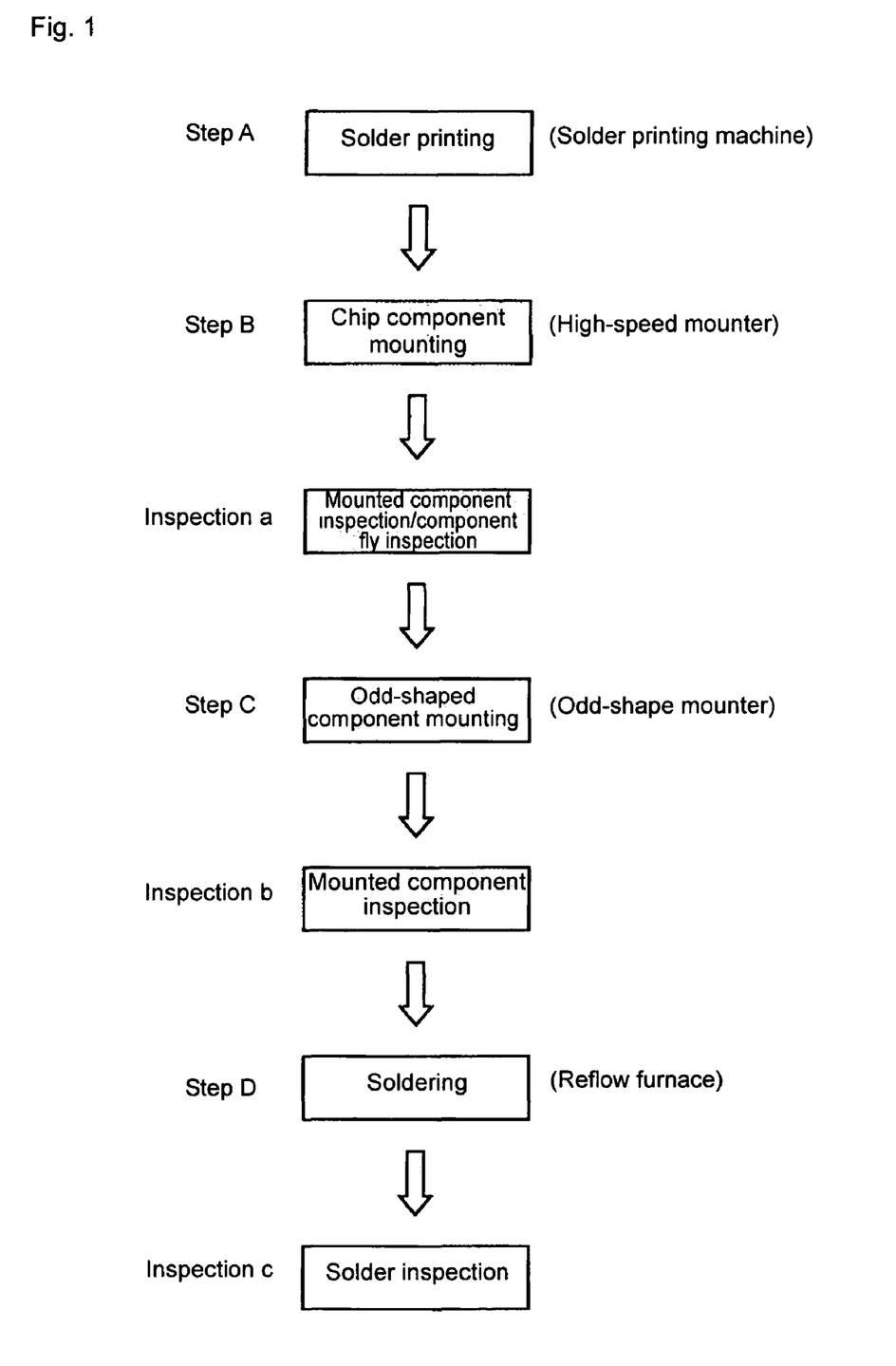
FIG. 1 shows an illustration showing a processing flow of a substrate fabricating line to which the present invention is applied.

FIG. 1 shows a flow of processing in a substrate fabricating line to which the present invention is applied.

In the substrate fabricating line of this embodiment, a component mounted substrate is completed in four steps A, B, C, and D and inspections a, b, and c are executed after the steps B, C, and D.

In the first step A, cream solder is printed on a printed circuit board by a solder printing machine. In the next step B, the solder-printed substrate is supplied to a high-speed mounter to mount a chip component. Moreover, in the step C, the substrate undergoing the step B is supplied to an odd-shape mounter to mount odd-shaped components such as BGA, CSP, and IC. In the final step D, the component-mounted substrate is sent into a reflow furnace to heat the substrate and fix each component on the substrate.

Inspections a, b, and c are performed by a substrate inspecting apparatus using a computer as its main control body. The inspection a executed between the steps B and C performs the inspection for determining on each chip component mounted in the step B whether the solder printed state and component mounted state are proper (hereafter referred to as "mounted component inspection") and moreover, executes component fly inspection to be described later. The inspection b executed between the steps C and D executes mounted component inspection for a odd-shaped component mounted in the step C. Moreover, the inspection c after the step D executes inspection (solder inspection) for determining on the soldered portion of each component whether the solder shape and tilted state are proper. A substrate passing the solder inspection is shipped as a final product.

When no-good determination is made in the inspection a or b, it is possible to temporarily stop the line in order to recollect the defective substrate. In this case, the recollected substrate is corrected for a no-good portion and then supplied to the same inspecting apparatus again or correction is confirmed by a person in charge and then sent to a downstream step.

Figure 2:
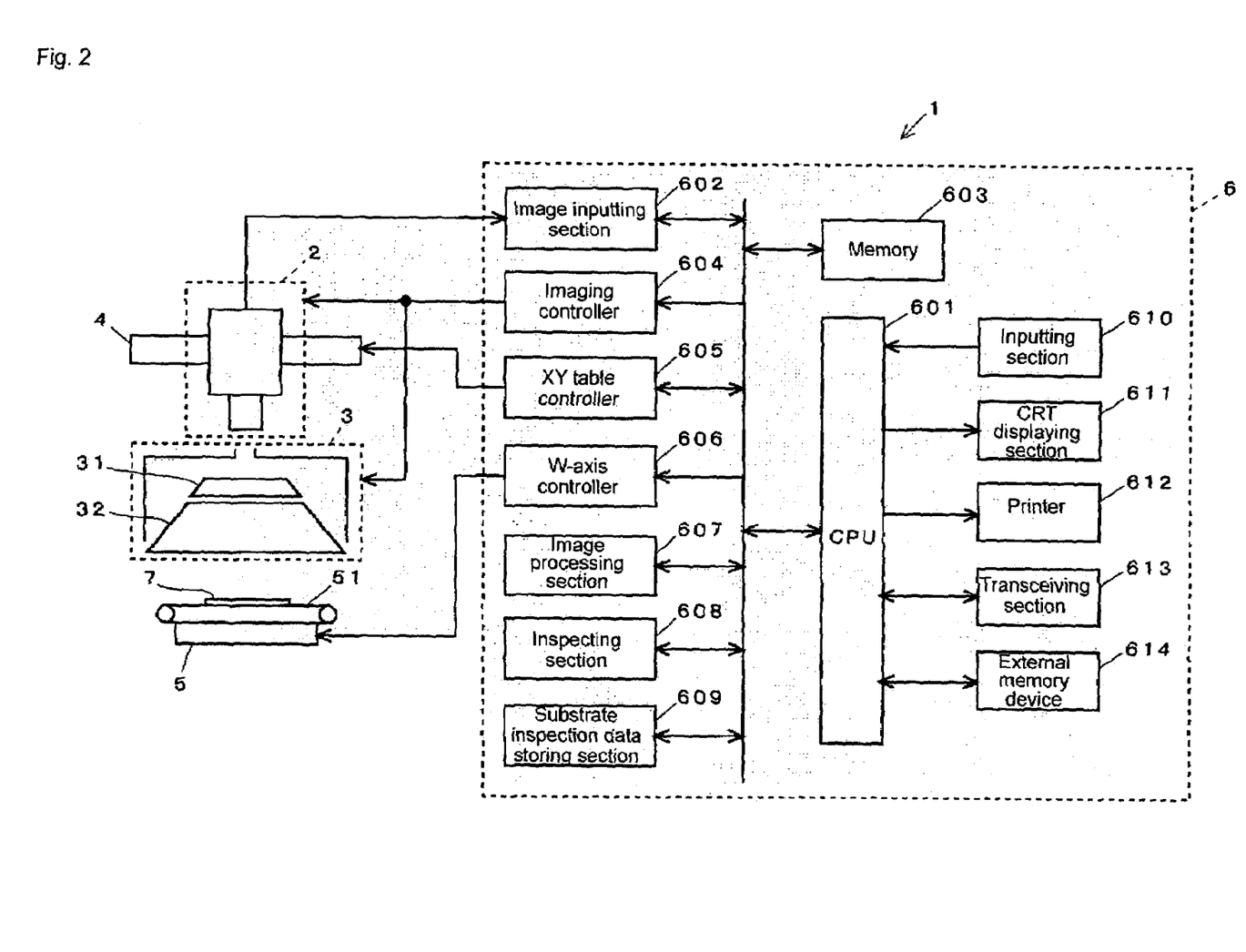
FIG. 2 shows a block diagram showing an electrical configuration of a substrate inspecting apparatus.

FIG. 2 shows a configuration of a substrate inspecting apparatus for executing the inspection a. The substrate inspecting apparatus 1 performs inspection by using an image obtained by imaging a substrate 7 to be inspected, which is constituted by an imaging section 2, projecting section 3, XY table section 4, substrate supporting section 5, and control processing section 6.

The XY-axis table section 4 is used to adjust an imaging position for the substrate 7 to be inspected, which moves the imaging section 2 and projecting section 3 along X-axis direction (horizontal direction in FIG. 2) and Y-axis direction (direction orthogonal to the paper surface in FIG. 2) while supporting the sections 2 and 3. The substrate supporting section 5 has a conveyer 51 for bringing in/out the substrate 7. The conveyer 51 is constituted so as to be able to adjust its width in accordance with the size of a substrate to be inspected.

The projecting section 3 is constituted by two annular light sources 31 and 32. The upper light source 31 emits red light and the lower light source 32 emits white light, which are arranged so as to be located in directions corresponding to different elevation angles viewed from the support face of the substrate 7 by adjusting the center to the position immediately above an observing position.

The imaging section 2 is a CCD camera for generating a color image, which is positioned so that the optical axis of the camera corresponds to the center of each light source and goes along the vertical direction.

The substrate inspecting apparatus 1 basically images an object with only white illumination by the lower light source 32. However, when it is necessary to observe a slope such as a solder printed pattern, an image in which solder is shone red is generated by also turning on the upper light source 31 to observe the shape and size of the red pattern.

The control processing section 6 is a computer using a CPU 601 as a main control body, which is constituted by an image inputting section 602, memory 603, imaging controller 604, XY table controller 605, W-axis controller 606, image processing section 607, inspecting section 608, substrate inspection data storing section 609, inputting section 610, CRT displaying section 611, printer 612, transceiving section 613, and external memory device 614.

The image inputting section 602 is provided with an input port for accepting image data values of R, G, and B supplied from the imaging section 2. The memory 603 stores digital image data values for R, G, and B and a binary image obtained by digitizing these image data values and moreover, it is used to temporality store information transmitted from the high-speed mounter and a midstream result of inspection.

The imaging controller 604 is provided with an interface for connecting the imaging section 2 and projecting section 3 to the CPU 601 to turn on each of the light sources 31 and 32 of the projecting section 3 in accordance with an instruction from the CPU 601, control the turning-off operation, and adjust luminous energy.

The XY table controller 605 includes an interface for connecting the XY table section 4 to the CPU 601 and controls movement of the XY table section 4 in accordance with an instruction from the CPU 601. The W-axis controller 606 is used to adjust the width of the conveyer 51 of the substrate supporting section 5 and moreover executes the control according to an instruction from the CPU 601.

The substrate inspection data storing section 609 is a memory for storing the substrate inspection data set for each type of substrate. Each substrate inspection data is constituted by storing the component inspection data for a chip component mounted on a corresponding substrate by a front-stage high-speed mounter in a data file provided with a predetermined file name (hereafter referred to as "inspection data file"). Moreover, the inspection data file of this embodiment stores inspection data for inspection for determining whether a chip component flies to the mounting position of an odd-shaped component to be mounted by the next odd-shape mounter (this is the component fly inspection previously described). Details of the component-fly inspection data will be described later.

The image processing section 607 extracts gradations of R, G, and B and the lightness shown by the total of these gradations in pixels by the digital image data values for R, G, and B stored in the memory 603. Moreover, at the time of inspection, the image processing section 607 executes processing of setting an inspecting window in accordance with the component inspection data and component fly inspection data for each component and extracting an image corresponding to the color of a component (hereafter referred to as "prospective image" of component) and processing of calculating the characteristic value of the extracted prospective image.

The inspecting section 608 performs quality determination by comparing the characteristic value extracted in the inspecting window with a criterion value every component and outputs the determination result to the CPU 601. The CPU 601 finally determines whether the substrate 7 is a good product in accordance with the determination result for each inspecting window. The final determination result is output to the CRT displaying section 611, printer 612, or transceiving section 613.

The inputting section 610 is used to input various conditions for inspection and inspection information, which is constituted by a keyboard and a mouse. The CRT displaying section 611 (hereafter merely referred to as "displaying section 611") accepts image data and inspection results from the CPU 601 and input data from the inputting section 610 and displays them on a display screen. Moreover, the printer 612 accepts inspection results from the CPU 601 and prints out the results in accordance with a predetermined format.

The transceiving section 613 is used to transfer data to and from an external device. It is possible to set the front- or rear-stage mounter or not-illustrated substrate-carrying-line controller as an external device.

The external memory device 614 is a reader-writer for a predetermined storing medium such as a flexible disk, CD-R, or magneto-optical disk, which is used to store the inspection results and capture programs and set data necessary for inspections from an external device.

In the above configuration, the image processing section 607 and inspecting section 608 are respectively constituted by an exclusive processor in which a program for executing the above processings is built. However, it is not always necessary to use an exclusive processor. It is allowed to provide functions of the image processing section 607 and inspecting section 608 for the CPU 601 for performing main control. Moreover, it is not individually physically set the memory 603 and substrate inspection data storing section 609. It is possible to set them in the same memory device (such as hard disk device).

In the above substrate inspecting apparatus 1, the component inspection data for the above chip component includes the coordinates and mounting direction (shown by tilt of component in predetermined reference direction) of a corresponding component, inspection-window setting data, binary threshold value (set for each of gradations R, G, and B and each lightness) necessary to extract the color of a chip component, and a criterion value for determining whether the prospective image of the component extracted in accordance with the binary threshold value exactly shows the component.

The above-described component-fly inspection data also includes inspection-window setting data, a binary threshold value, and a criterion value the same as the chip-component inspection data does. However, the above inspecting window is a window corresponding to the mounting position and size of each odd-shaped component. Moreover, the binary threshold value is set as a threshold value adapted for these components in common and a threshold value individual for each component. Furthermore, the criterion value is used for processing of determining whether the image of a component is present in an inspecting window. In the case of this embodiment, a value showing the size of a component is set.

Figure 3:
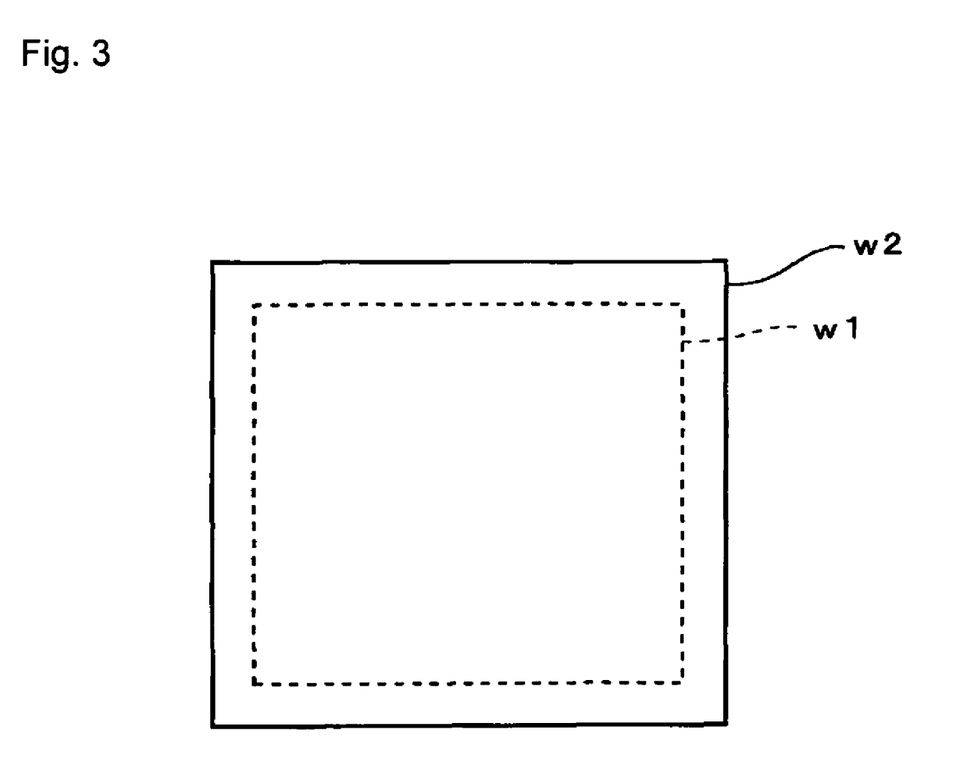
FIG. 3 shows an illustration showing a set example of an inspection window.

FIG. 3 shows a set example of an inspecting window. In FIG. 3, symbol w1 denotes a component body window corresponding to the body of the component, which is used to confirm presence or absence of the component in original mounted-component inspection. Symbol w2 denotes a window for inspecting component fly, which is set in accordance with the component body window w1.

Figure 4:
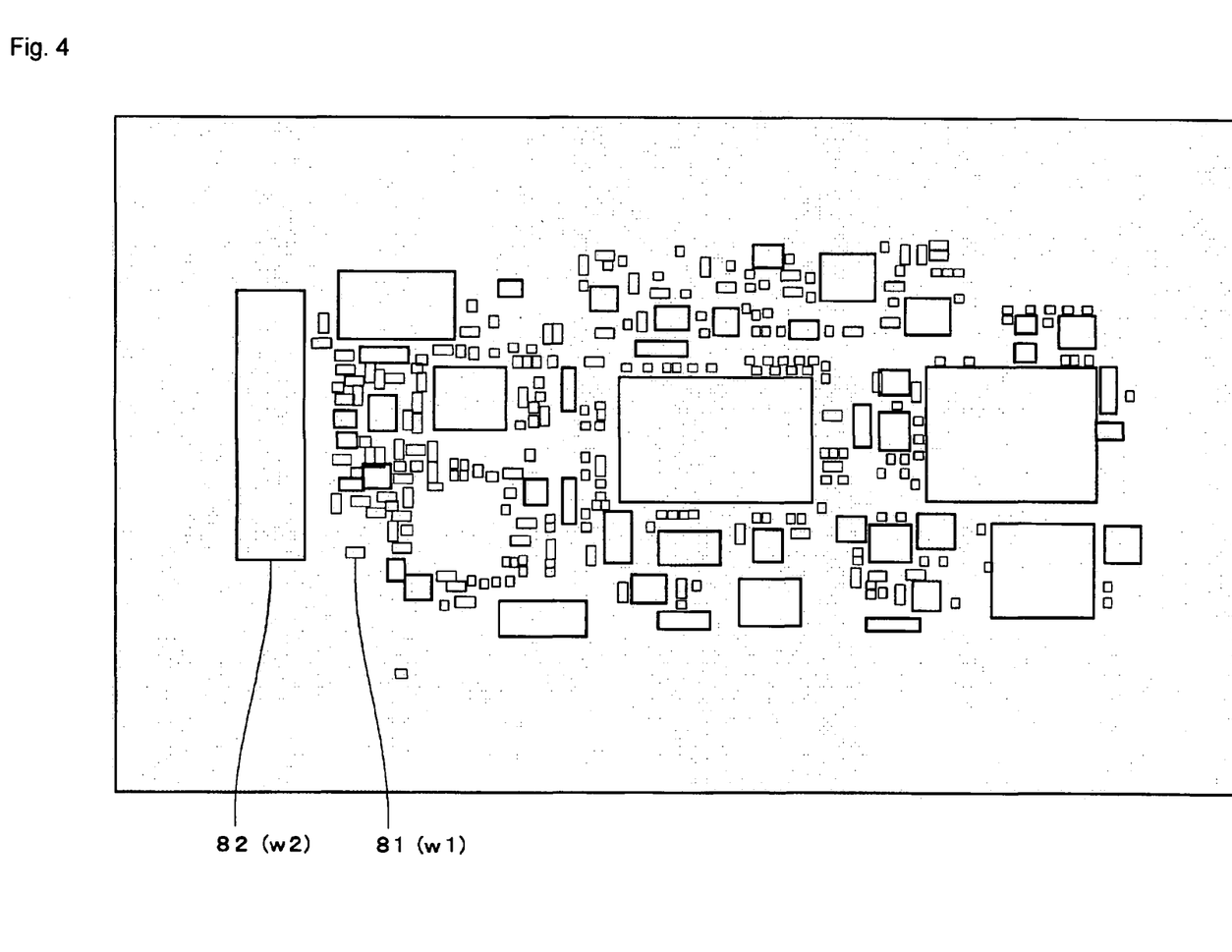
FIG. 4 shows an illustration showing a distribution state of inspection windows.

FIG. 4 shows a distribution of inspecting windows same as the above inspecting window. In FIG. 4, a small rectangle 81 drawn by a thin line denotes a window for inspecting a component mounted on a chip component, which is constituted by the component body window w1 for each chip component. A rectangle 82 drawn by a thick line, however, denotes a window for inspecting the component fly, which is constituted by the window w2 obtained by enlarging the component body window wi for an odd-shaped component.

The component-fly inspection data of this embodiment includes the set data of the window w1 together with the set data of the window w2 to confirm the component position. However, without being restricted to the above mentioned, it is also allowed to include only the set data of the window w2.

Figure 5A:
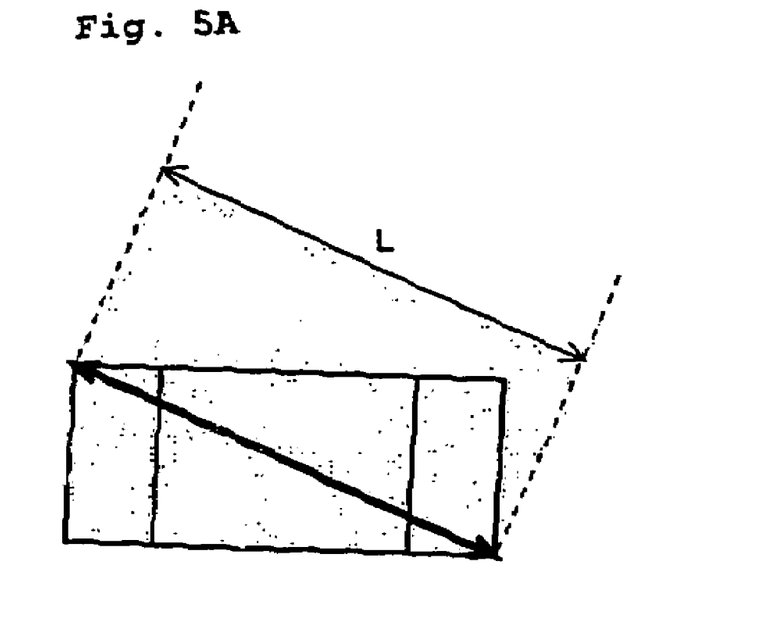
FIGS. 5A and 5B show illustrations showing set examples of criterion values used for component fly inspection.
Figure 5B:
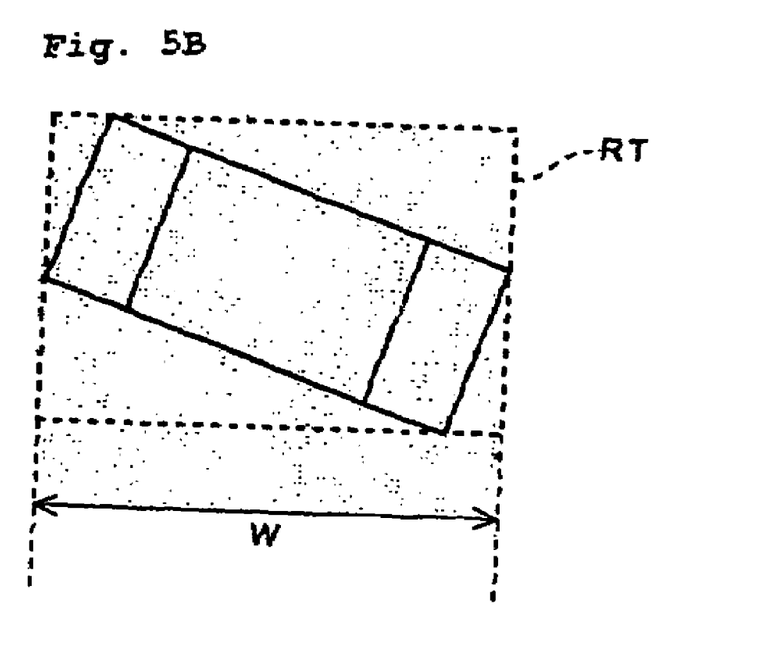

FIG. 5 shows a set example of a criterion value for performing determination processing according to the size of a component in component fly inspection.

FIGS. 5A and 5B show a set example of a criterion value for performing determination processing according to the size of a component in component fly inspection.

When component fly occurs, the flied chip component is in a state of turning to any direction. Therefore, in the case of this embodiment, a circumscribing rectangle RT is set for a prospective image of a component extracted in accordance with a binary threshold value as shown in FIG. 5A so as to express the size of the component by the length of the major side W (W is hereafter referred to as "component width W") of the rectangle RT.

Moreover, in the case of this embodiment, the criterion value for the component width W is expressed by a ratio to the length L shown in FIG. 5B. The length L denotes the length of the diagonal line of the image of a chip component, which is previously obtained by measuring the image of a model chip component. Because the ratio to the length L depends on the direction of the flied component, the minimum value L1 and maximum value L2 of the fluctuating numerical value range are set as criterion values in this embodiment. That is, when the prospective image of the component extracted in the inspecting window is a chip component, the component width W satisfies the condition of $L1 \leq W \leq L2$.

Furthermore, in the case of this embodiment, numerical values showing the range of the area of a component are also set as the above criterion values. For the area, only the maximum value $S_{max}$ is set. When the prospective image of a component in an inspecting window is a chip component, the area S satisfies the condition of $S \leq S_{max}$. In the case of component fly inspection, conditions of the component width W and area S are both satisfied, it is determined that a prospective image expresses a chip component.

Because chip components to be mounted on a substrate have a plurality of sizes, it is preferable to set criterion values for the component width and area for each size. In the case of component fly inspection, characteristic values of a prospective image extracted through digitization are successively compared with the criterion value for each size. Moreover, when a plurality of prospective images is extracted in one inspecting window, it is necessary to execute processing of comparing the characteristic value of each prospective image with a criterion value.

Moreover, because a plurality of colors is used depending on the type of a chip component, it is preferable to set a binary threshold value for each of the colors and successively extract a prospective image corresponding to each color in accordance with these binary threshold values. Furthermore, to extract the component width W and area S, it is preferable to set a body-extracting binary threshold value and an electrode-portion-extracting binary threshold value for each type of chip component.

Then, it is not always necessary to execute the above component fly inspection for all substrates. It is allowed to execute the component fly inspection only when it is clear that component fly occurs or the possibility of component fly is high. A case in which it is clear that component fly occurs can be considered as a case in which it is detected that a chip component is missing. Moreover, a case in which the possibility of component fly is high can be considered as a case in which the attracting nozzle of a high-speed mounter is abraded and a malfunction easily occurs in attraction or cancel of the attraction of a component.

Therefore, in the case of this embodiment, the following conditions 1, 2, and 3 are set as conditions for executing component fly inspection for the substrate inspecting apparatus, a user selects a condition suitable for the actual situation of the substrate fabricating line out of these conditions, and the component fly inspection is executed when the selected condition is effected.

Condition 1: When it is detected that a component is missing in mounted component inspection.

Condition 2: When the replacement date of the attracting nozzle of a high-speed mounter is approaching.

Condition 3: When all substrates are to be inspected.

In the above conditions, the condition 1 corresponds to the above case in which component fly securely occurs and the condition 2 corresponds to the above case in which the possibility that component fly occurs is high. However, the condition 1 cannot correspond to a case in which a component other than a component to be originally mounted is flown such as a case in which an attracting nozzle attracts two components. Also, the condition 2 cannot correspond to a case in which component fly occurs due to malfunction though an attracting nozzle is not abraded.

In the case of the condition 3, however, it is possible to most securely detect component fly because component fly inspection is executed for all substrates to be inspected without restricting conditions. Therefore, a user capable of specifying the factor of component fly can execute efficient inspection by selecting the condition 1 or 2. However, it is preferable that a user not able of specifying the factor of component fly takes a safety measure of detecting a trouble due to component fly at a high accuracy though inspection time increases by selecting the condition 3.

In the case of this embodiment, when the condition 2 is selected, it is determined whether the condition 2 is effected by capturing a signal showing that the replacement date of an attracting nozzle is approaching (hereafter referred to as "warning signal") or a signal showing that replacement of an attracting nozzle is completed (hereafter referred to as "cancel signal") from an upstream high-speed mounter. The warning signal is output when the number of operation times of an attracting nozzle is counted by a high-speed mounter and the counted value reaches a predetermined number of operation times. The cancel signal is output when a person in charge confirms the attracted state of a component after replacing an attracting nozzle and performs the replacement completion operation in accordance with the operation.

Figure 6:
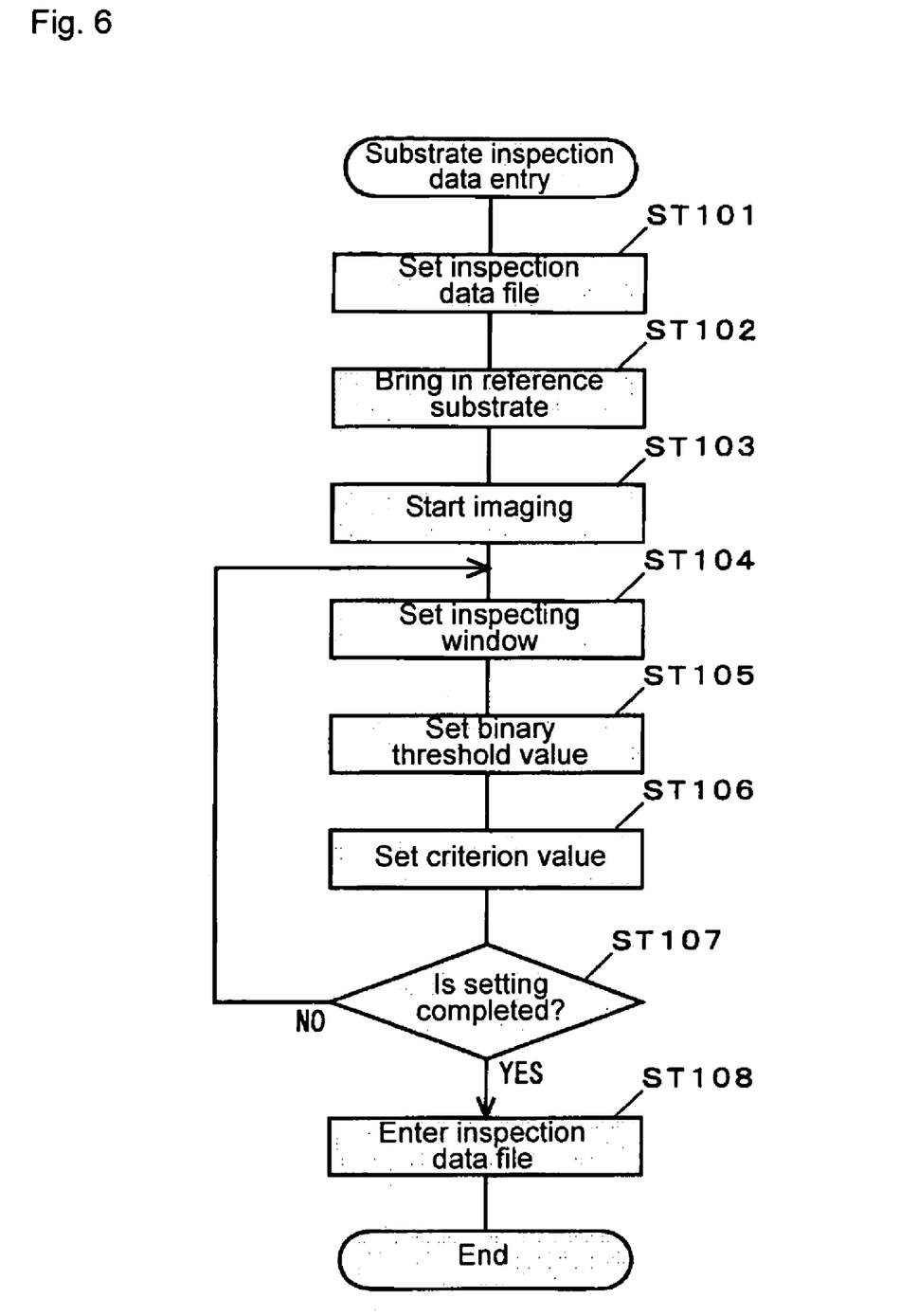
FIG. 6 shows a flowchart showing a procedure for entering substrate inspection data.
Figure 7:
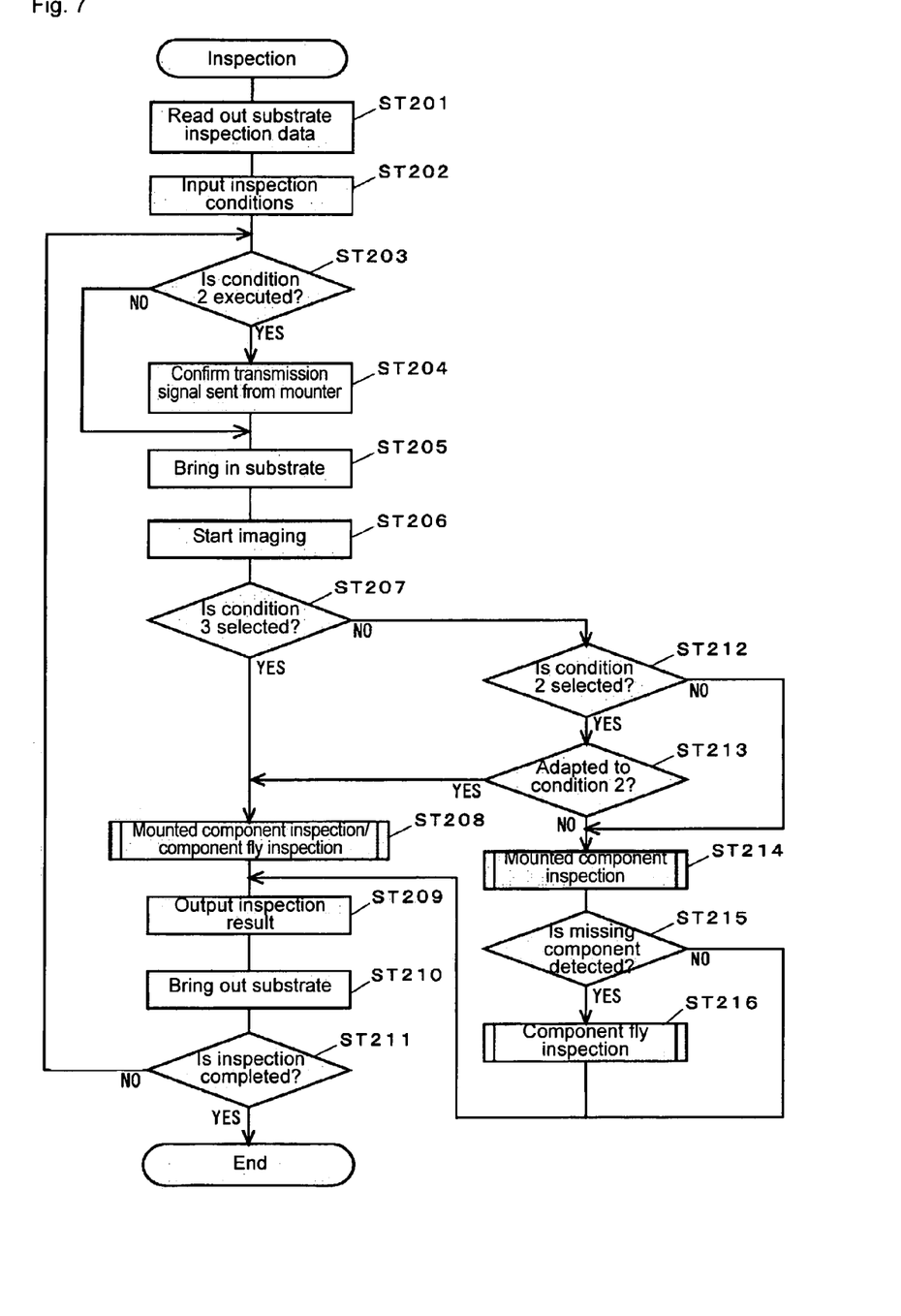
FIG. 7 shows a flowchart showing a procedure of substrate inspection.

Then, the procedure of processing to be executed by the above substrate inspecting apparatus is described below by referring to FIGS. 6 and 7. FIG. 6 shows a procedure for generating and entering substrate inspection data, in which each step (ST) is shown by a numeral between 101 and 108 (both included). Moreover, FIG. 7 shows a procedure for inspection, in which each step is shown by a numeral between 201 and 216 (both included).

First, substrate inspection data is generated by using a model substrate in which each chip component is mounted at a correct position (this substrate is hereafter referred to as "reference substrate"). The procedure in FIG. 6 is started in accordance with an operation that an operator inputs a predetermined file name. In ST101, a vacant inspection data file provided with an input file name is set to the memory 603. Then, the operator sets the reference substrate to a predetermined position and performs the start operation, the reference substrate is carried onto the substrate supporting section 5 in ST102 and then, imaging by the imaging section 2 is started in ST103.

An image sent from the imaging section 2 is output to the displaying section 611 through the image inputting section 602 and CPU 601. The operator sets an inspecting window, binary threshold value, and criterion value in order every portion to be inspected while confirming the image display at the displaying section 611 (ST104, ST105, and ST106). In this case, when a portion to be inspected is a chip-component mounting position, the inspection data specific to a chip component to be mounted is set in ST104 to ST106. However, when a portion to be inspected is an odd-shaped-component mounting position, in ST104 to ST106, binary threshold values for extracting a plurality of colors and criterion values corresponding to a plurality of sizes are set in order to execute the above component fly inspection.

Thus, the above three types of inspection data values are successively set to all inspecting portions in an input image. While the loop of ST104 to ST107 is repeated, the set data is stored in an inspection data file temporarily stored in the memory 603.

When setting all portions to be inspected is completed and the set completion operation is performed, ST107 becomes "YES" and ST108 is started, and the inspection data file is entered in the substrate inspection data storing section 609 to complete processing.

To set a binary threshold value in ST105, when a portion to be inspected is a chip component, it is possible to automatically set threshold values in accordance with values of R, G, and B, and lightness corresponding to colors at designated positions in accordance with an operation for an operator to designate a chip component on an image. However, when a potion to be inspected is a odd-shaped component, it is also allowed to accept an operation of temporarily designating a chip component outside an inspecting window because there is not any color to be designated in the inspecting window. In this case, the CPU 601 can successively accept designations for a plurality of types of chip components, set a binary threshold value adapted for every chip component, and link the value to the inspecting window.

Moreover, in the case of the above inspection data setting, by first completing setting the inspection data for inspecting a mounted component and then setting the inspection data for inspecting component fly, it is possible to select a binary threshold value adapted for component fly inspection from binary threshold values set for mounted component inspection of various types of chip components. Moreover, it is possible to use a set value for mounted component inspection as a criterion value.

Furthermore, though various inspection data values are set in accordance with operations by an operator in the case of the procedure in FIG. 6, it is also possible to generate an inspection data file by previously setting and entering the standard inspection data for each component and linking the entered data with the substrate design data such as CAD data.

Then, the inspection procedure in this embodiment is described below.

An operator designates the type of a substrate to be inspected in accordance with a substrate name or the like at the start of inspection. The procedure in FIG. 7 is started in accordance with the above designation. First, in ST201, the substrate inspection data for the designated substrate is read out and set to the memory 603. Moreover, this embodiment accepts the input of the above condition for component fly inspection in ST202 and the input can be executed by displaying the conditions 1, 2, and 3 on the displaying section 611 and inputting options corresponding to the conditions (for example, shown by numerals 1, 2, and 3).

In this case, when the condition 2 is selected, that is, when it is designated to execute component fly inspection by premising that the replacement date of the attracting nozzle of the high-speed mounter is approaching, ST203 becomes "YES" and presence or absence of a transmission signal from is confirmed in the next ST204. Moreover, when the signal is transmitted, the content of the signal is confirmed. When the condition 1 or 3 is selected, ST203 becomes "NO" and ST204 is skipped.

When the inspection start operation is executed under the above state, bring-in of the first substrate is accepted in ST205 and imaging by the imaging section 2 is started in ST206.

In this case, when it is assumed that the condition 3 is selected in ST202, the next ST207 becomes "YES" and ST208 is started to execute both mounted component inspection and component fly inspection.

In ST208, portions to be inspected on an image are noticed in an optional sequence to execute the inspection corresponding to each portion. That is, when a noticed portion is the mounting position of a chip component, mounted component inspection of the chip component is executed and when a noticed portion is the mounting position of an odd-shaped component, component fly inspection is executed. In the case of actual substrate inspection, a plurality of times of imaging is frequently performed while changing imaging positions. However, as described above, according to the processing of executing two types of inspections by mixing them, it is possible to input the next image after processing all inspecting windows included in the same image and execute efficient inspections.

When inspections for all portions to be inspected are completed, ST208 is completed and ST209 is started to output the inspection results to the displaying section 611 and transceiving section 613. In the next ST210, substrates to be inspected are brought out to the line at an odd-shape mounter. Thereafter, when there is a substrate to be next inspected, ST203 is restarted to start the inspecting procedure for the next substrate. The procedure for returning to ST203 from ST209 to ST211 and ST211 is the same as the case in which the other condition 1 or 2 is selected.

Thus, when the condition 3 is selected, both mounted component inspection and component fly inspection are executed whenever a substrate is brought in.

However, when the condition 1 is selected, a substrate is brought in ST205, imaging is started in ST206, and then both ST207 and ST212 become "NO" and ST214 is started to execute only mounted component inspection of a chip component. When the inspection is completed, it is checked in ST215 whether it is detected that a component is missing in the above inspection. When this determination is "NO", the above ST209 is started after ST215. However, when it is detected that a component is missing, ST215 becomes "YES" and ST216 is started to execute component fly inspection and then, ST209 is started.

Therefore, when the condition 1 is selected, mounted component inspection of a chip component is executed whenever a substrate is brought in and when it is detected that a component is missing in this inspection, component fly inspection is executed.

Then, when the condition 2 is selected, steps ST205 and ST206 are executed, then ST207 becomes "NO", and ST212 becomes "YES", and ST213 is started to determine whether the current state is a state adapted for the condition 2. The determination in ST213 is performed in accordance with the content of a signal transmitted from a high-speed mounter in ST204 before a substrate is brought in.

In the period until a warning signal is accepted from a high-speed mounter, ST213 becomes "NO" to execute mounted component inspection of a chip component in ST214 for each substrate to be inspected the same as the case of the condition 1. In the case of this embodiment, even if selecting the condition 2, it is checked in ST215 whether it is detected that a component is missing after the mounted component inspection and when it is detected that the component is missing, component fly inspection is executed in ST216.

When a warning signal is accepted from a high-speed mounter at a predetermined point of time, the above ST213 becomes "YES". Thus, when determination of "YES" is made in ST213, ST208 is started to execute mounted component inspection and component fly inspection in parallel the same as the case in which the condition 3 is selected.

Thus, after completing the inspection for the substrate immediately after accepting the warning signal, a substrate to be next brought in is also determined as "YES" in ST213. Moreover, when outputting a signal by a high-speed mounter, this embodiment accepts a cancel signal showing that replacement of nozzles is completed after receiving a warning signal by considering the possibility that a predetermined number of substrates is already present on the line from the mounter up to a substrate inspecting apparatus and moreover, continues determination of "YES" in ST213 until inspection of substrates which may be carried on the line from the high-speed mounter when receiving the signal is completed. While the "YES" determination continues, both mounted component inspection and component fly inspection are executed for substrates brought in every hour.

When accepting the cancel signal and processing of the substrates which may be carried on the line from the high-speed mounter is completed, the determination in ST213 when accepting the next substrate becomes "NO". Therefore, after the determination processing in ST213, ST214 is restarted and only the mounted component inspection of chip components is executed as long as it is not detected that a component is missing.

Therefore, when the condition 2 is selected, both mounted component inspection and component fly inspection are executed for substrates undergoing mounting processing during the period in which it is necessary to replace attracting nozzles at the high-speed mounter.

Moreover, it is allowed to set a condition of "performing component fly inspection during the period in which it is necessary to replace implements such as a mask and squeezee in a solder printing machine" in addition to the above three types of conditions. When setting the above condition, it is preferable to accept a warning signal and cancel signal same as the case of the high-speed mounter from the solder printing machine and progress inspections in accordance with the same procedure as the case of the condition 2.

Moreover, though a region to be inspected for component fly inspection is restricted to a region corresponding to the mounting position of an odd-shaped component in the case of the above embodiment, without being restricted to the above mentioned, it is also allowed to executed component fly inspection for the whole image excluding the mounting position of a chip component.

In the case of the fabricating line shown in FIG. 1, the step B for mounting a chip component is executed by a high-speed mounter and the step C for mounting a odd-shaped component is executed by a odd-shape mounter. However, without being restricted to the above mentioned, it is also possible to execute the steps B and C by a modular-type mounter. In this case, it is possible to set a fabricating line in which a plurality of modular-type mounters is allocated to the step B requiring high-speed processing, for example, two mounters are used for the step B while executing the step C by one mounter. Also in this fabricating line, it is possible to execute inspections same as the case of the above embodiment for a substrate passing through the final mounter in the step B.

According to the present invention, it is possible to inspect whether a component mounted in a first component mounting step is flied to a component mounting position in the next second component mounting step. Therefore, it is possible to prevent a substrate in which the above component fly occurs from being sent to the second component mounting step.

What is claimed is:

1. A substrate inspecting method to be executed between a first component mounting step of mounting a predetermined type of component on a substrate and a second component mounting step of mounting another component on a mounting area of the substrate on which no component is mounted in the first component mounting step, the method comprising:
    inspecting the substrate that has undergone the first component mounting step, to determine whether or not the component mounted in the first component mounting step is improperly positioned so as to at least cover the mounting area for the another component to be mounted in the second component mounting step.

2. The substrate inspecting method according to claim 1, further comprising:
    a processing of imaging a substrate that has undergone the first component mounting step whenever accepting the substrate;
    a first inspection for determining on an obtained image whether the image of a component is included in a region corresponding to the component mounting position in the first component mounting step; and
    a second inspection for determining whether the image of a component mounted in the first component mounting step is included in a region corresponding to the component mounting position in the second component mounting step.

3. The substrate inspecting method according to claim 1, further comprising:
    a processing of imaging a substrate that has undergone the first component mounting step whenever accepting the substrate;
    a first inspection for determining on an obtained image whether the image of a component is included in a region corresponding to the component mounting position in the first component mounting step; and a second inspection for determining whether the image of a component mounted in the first component mounting step is included in a region corresponding to the component mounting position in the second component mounting step when it is determined in the first inspection that the image of a component is not correctly included in a predetermined region.

4. The substrate inspecting method according to claim 1, wherein processing of imaging a substrate undergoing the first component mounting step and first inspection for determining whether the image of a component is included in a region corresponding to the component mounting position in the first component mounting position in the first component mounting step are executed whenever accepting the substrate under a state in which it is possible to accept the information showing the expiry date of a component-mounting implement used in the first component mounting step, and wherein, correspondingly to input of the information, the method further comprising:

a second inspection for determining whether the image of a component mounted in the first component mounting step is included in a region corresponding to the component mounting position in the second component mounting step is executed for a predetermined number of substrates to be subsequently accepted together with the imaging and the first inspection.

5. The substrate inspecting method according to claim 1, wherein processing of imaging a substrate undergoing the first component mounting step and first inspection for determining whether the image of a component is included in a region corresponding to the component mounting position in the first component mounting position in the first component mounting step are executed whenever accepting the substrate under a state in which it is possible to accept the information showing that a solder printed state of the substrate is deteriorated, and wherein, correspondingly to input of the information, the method further comprising:

a second inspection for determining whether the image of a component mounted in the first component mounting step is included in a region corresponding to the component mounting position in the second component mounting step is executed for a predetermined number of substrates to be subsequently accepted together with the imaging and the first inspection.

6. The substrate inspecting method according to claim 1, wherein the first component mounting step is a step of mounting a chip component.

7. The substrate inspecting method according to claim 1, wherein the second component mounting step is a step of mounting an odd-shaped component.

8. A substrate inspecting method for inspecting a component previously mounted on a substrate, the method comprising:

a) inspecting the component previously mounted on the substrate by fly inspection, to determine whether or not the component mounted is improperly mounted so as to at least partly cover a mounting area for a component to be mounted at a later point in time, b) if it is determined by the step a) that the component is improperly mounted, outputting an error signal to signify that the component needs to be removed and remounted.

9. The substrate inspecting method according to claim 8, further comprising:

c) if it is determined by the step a) that the component is properly mounted, mounting another component on the substrate, wherein the another component corresponds to a component having an odd shape and wherein the component mounted has a normal shape;

d) inspecting the another component mounted in the step d), to determine whether or not the another component mounted in the step d) is improperly mounted, wherein the component is mounted by a high-speed mounter and the another component mounted in the step c) is mounted by an odd-shape mounter.

10. The substrate inspecting method according to claim 8, wherein the step a) comprises:

a1) shining light sources of at least two different colors on a portion of the substrate corresponding to where the component should have been mounted;

a2) generating a color image from the light sources of least two different colors shone on the substrate;

a3) comparing the color image obtained in the step a2) to stored data corresponding to a proper inspection position of the component, in order to determine if the component has been mounted properly.

11. The substrate inspecting method according to claim 9, wherein the inspecting step a) is performed by comparing the color image obtained in the step a2) with a first predetermined inspecting window, and wherein the inspecting step d) is performed by comparing a color image obtained during the inspecting step d) with a second predetermined inspecting window that is slightly larger in size than the first predetermined inspecting window.

12. The substrate inspecting method according to claim 11, wherein the first and second predetermined inspecting windows are rectangular in shape.

13. A substrate inspecting method, comprising:

a) setting an inspecting condition for substrates as either: 1) detecting a component that is missing in a mounting process of the substrates; 2) replacement date of an attracting nozzle used in the mounting process of the substrates is approaching; or 3) all of the substrates are to be inspected;

b) read out substrate inspection data and store in a memory;

c) if inspecting condition 2) is set, confirm that the attracting nozzle replacement date is approaching;

d) image a substrate;

e) if inspecting condition 3) is set, perform both mounted component inspection and component fly inspection on the substrate, and output an inspection result;

f) if inspecting condition 3) is not set and if inspecting condition 2) is not set, which corresponds to inspecting condition 1) being set, perform only mounted component inspection on the substrate, determine if a missing component is detected, and if a missing component is detected, perform component fly inspection and output an inspection result based on both the mounted component inspection and the component fly inspection, and if a missing component is not detected, output an inspection result based only on the mounted component inspection; and g) if inspecting condition 3) is not set and if inspecting condition 2) is set, perform both mounted component inspection and component fly inspection on the substrate, and output an inspection result.

14. The substrate inspecting method according to claim 13, further comprising, if inspecting condition 3) is not set and if inspecting condition 2) is set, determining whether a current state of a mounting system performing mounting of components on the substrate is adapted for inspecting condition 2), and if so, performing both mounting component inspection and component fly inspection on the substrate.

15. The substrate inspecting method according to claim 13, wherein the image step d) is performed by shining lights of at least two different colors on the substrate and obtaining a color image from the substrate as a result.

* * * * *